United States Patent [19]

Frazer et al.

[11] Patent Number: 5,155,023
[45] Date of Patent: Oct. 13, 1992

[54] ENZYME IMMUNOASSAY PROCEDURE FOR AMPHIPATHIC ANALYTES

[75] Inventors: John M. Frazer, Chula Vista; William B. Freese; Michael S. Voegtline, both of San Diego, all of Calif.

[73] Assignee: Synbiotics Corporation, San Diego, Calif.

[21] Appl. No.: 478,156

[22] Filed: Feb. 9, 1990

[51] Int. Cl.$^5$ .......................................... G01N 33/571
[52] U.S. Cl. .................... 435/7.36; 435/7.5; 435/7.92; 435/961; 436/518; 436/174
[58] Field of Search ..................... 435/7.36, 7.92, 7.94, 435/961, 962, 7.5; 436/510, 518, 528, 529, 530, 548, 811, 826, 174

[56] References Cited

U.S. PATENT DOCUMENTS 4,362,531 12/1982 de Steenwinkel et al. ......... 436/512
4,916,057 4/1990 Thompson et al. ................. 436/510

FOREIGN PATENT DOCUMENTS 303515 2/1989 European Pat. Off. .

OTHER PUBLICATIONS

Mearns et al., "Sensitive Immune Dot Blot Test for Diagnosis of *Chlamydia trachomatis* Infection", J. Clin. Microbiol. 26(9), pp. 1810-1813 (Sep. 1988).
Wilchek et al., "Review: The Avidin-Biotin Complex in Bioanalytical Applications", Anal. Biochem. 171(1), pp. 1-32 (May 15, 1988).

*Primary Examiner*—Esther L. Kepplinger
*Assistant Examiner*—Carol E. Bidwell
*Attorney, Agent, or Firm*—Edward S. Irons

[57] ABSTRACT

Immunoreagents for the release, non-specific capture and detection of lipopolysaccharides (LPS) that may be diagnostic for microorganisms causative for, among other things, *Chlamydia trachomatis* or *Chlamydia psittaci* are described.

5 Claims, 2 Drawing Sheets

ENZYME IMMUNOASSAY PROCEDURE FOR AMPHIPATHIC ANALYTES

FIELD OF THE INVENTION

This invention relates to an improved enzyme immunoassay for amphipathic analytes. More particularly, the invention relates to immunoreagents for the release, non-specific capture and detection of lipopolysaccharides (LPS) that may be diagnostic for microorganisms causative for, among other things, *Chlamydia trachomatis* or *Chlamydia psittaci*.

BACKGROUND OF THE INVENTION

It is known to form an immunological "sandwich" wherein an antibody is attached in a stable association with a solid surface, such as an absorbent membrane or microtitre well. The analyte is then free to interact with an antibody forming a high affinity complex. A second labeled antibody with specificities for the analyte is bound to this complex to form the immunological sandwich. This method of capturing analytes immunologically is frequently efficient in binding trace quantities in a background matrix. Further, this stable complex tends to allow extensive washing to remove interfering substances found in the matrix.

Certain analytes, such as *C. trachomatis* LPS, primarily because of their small size, do not lend themselves well to forming such an immunological sandwich. The epitope of such analytes is not sufficiently large (for example 3.5 kd in *C. trachomatis*) to easily bind the two antibodies. Consequently, a non-immunological form of analyte capture is often employed.

Other microbial LPS molecules of a much higher molecular weight that would be amenable to the typical sandwich assay might also be captured by a similar non-specific mechanism. Such non-specific forms of capture, because of much smaller analyte binding affinities, are not often as efficient in capturing sufficient analyte for detection especially when these analytes are present in low concentrations. The result is lower potential assay sensitivities. The antibody and enzyme conjugate reagents must be optimized in such a way as to enhance signal production. This often results in decreasing the specific signal with respect to background signal.

The prior art has attempted to minimize interference and optimize potential signal in such non-specific analyte capture by, among other methods, choosing release reagents which chemically or enzymatically degrade interfering substances, selecting pre-filters of such a composition that non-specific adsorption of analyte is minimized, and selecting or pre-treating capture surfaces such as to optimize non-specific binding. Since on one hand, non-specific adsorption onto surfaces and pre-filters need to be minimized, and on the other, non-specific binding to the capture surface increased, these methods are often compromising and result in poor potential sensitivities and specificities.

The specificity of an immunoassay is highly dependent upon he efficiency by which an antibody reacts with the analyte in question but not with other similar analytes. If certain potentially interfering organisms demonstrate the ability to bind the antibodies in question by mechanisms not involving the hypervariable region, such as associating with the carbohydrate or Fc regions, screening for non-crossreacting antibodies may become extremely difficult if not impossible.

Other methods of increasing the potential specificity of immunologically based assays include designing competition assays which quantify immunological interactions in an attempt to exclude cross reactants which often, but not always, have a weaker affinity for the antibody in question.

SUMMARY OF THE INVENTION

This invention provides an enzyme immunoassay (EIA) having improved theoretical sensitivity and specificity for amphipathic analytes in various background matrices of clinical origin.

The improvement is achieved by a chemical process involving, in a first step, a release reagent effective to separate the analyte from the matrix in non-reactive and stable form thus permitting the background matrix to be filtered off or modified in order to decrease interference. In a second step, another reagent, preferably guanidine, changes the analyte into a reactive conformation adherent to a capture surface. In one embodiment of the invention the release reagent yields a polar LPS intermediate and the second reagent converts the intermediate into a non-polar LPS.

The release reagent functions may include, but are not limited to: 1) solubilization of and dispersion of mucopolysaccharides which could otherwise interfere with the performance of immunoassays, 2) denaturation and/or precipitation of proteins and other macromolecules which could otherwise interfere with the assay, 3) disruption of biological complexes for the purpose of exposing analyte epitopes required for immunological detection.

The release reagent may also induce and stabilize a macromolecular analyte conformation which minimizes the loss of potential sensitivity through non-specific binding during manipulations such as dispensing and pre-filtration.

The purposes of the second reagent include, but are not limited to, the modification of the macromolecular conformation of the analyte product of the first step to render it reactive with a capture surface which has been previously treated to enhance its affinity for the analyte.

This invention also includes chemical modification of the antibody which is used for the detection of the analyte. This modification results in the significant reduction in the non-specific reaction with undesired cross-reactants without significantly decreasing the interaction with the desired analyte.

This modification involves the oxidative cleavage of the vicinal hydroxyl groups in the carbohydrate residues into reactive aldehydes. The aldehydes are subsequently reacted with biotin hydrazide to form stable biotinylated antibodies. The non-specific cross-reactivity of such modified antibodies have been found to be significantly reduced.

DESCRIPTION OF THE INVENTION

Figure 1:
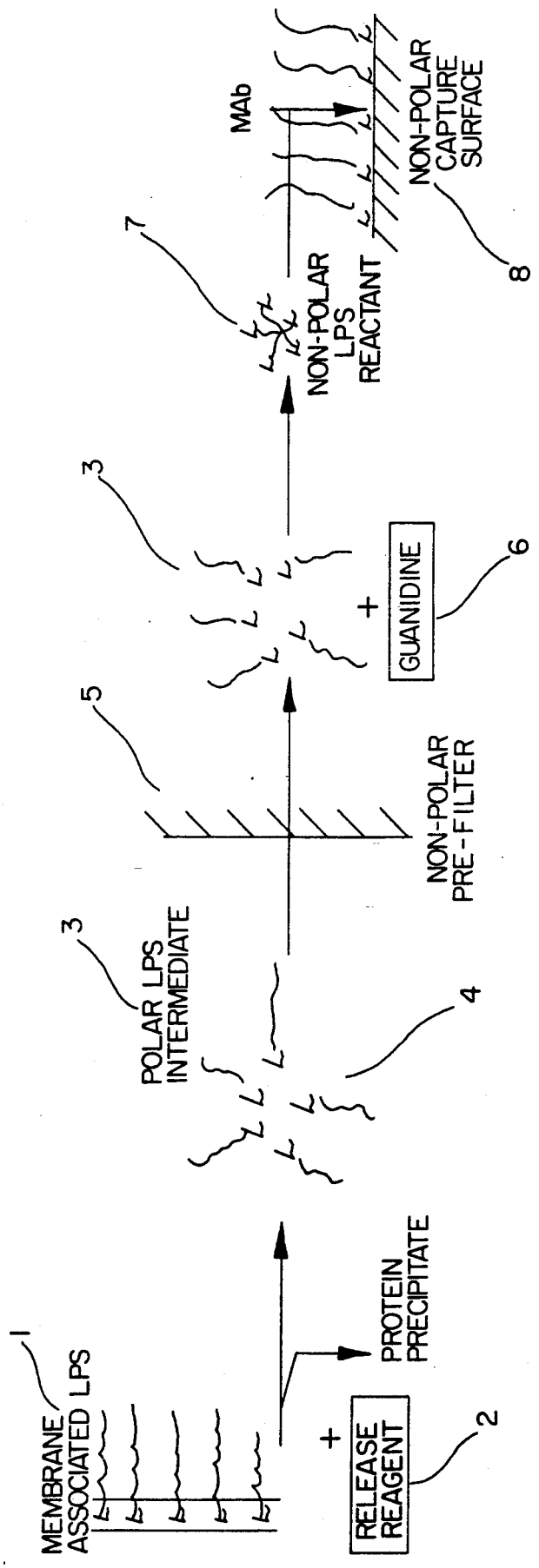
FIG. 1 illustrates an LPS.
Figure 2:
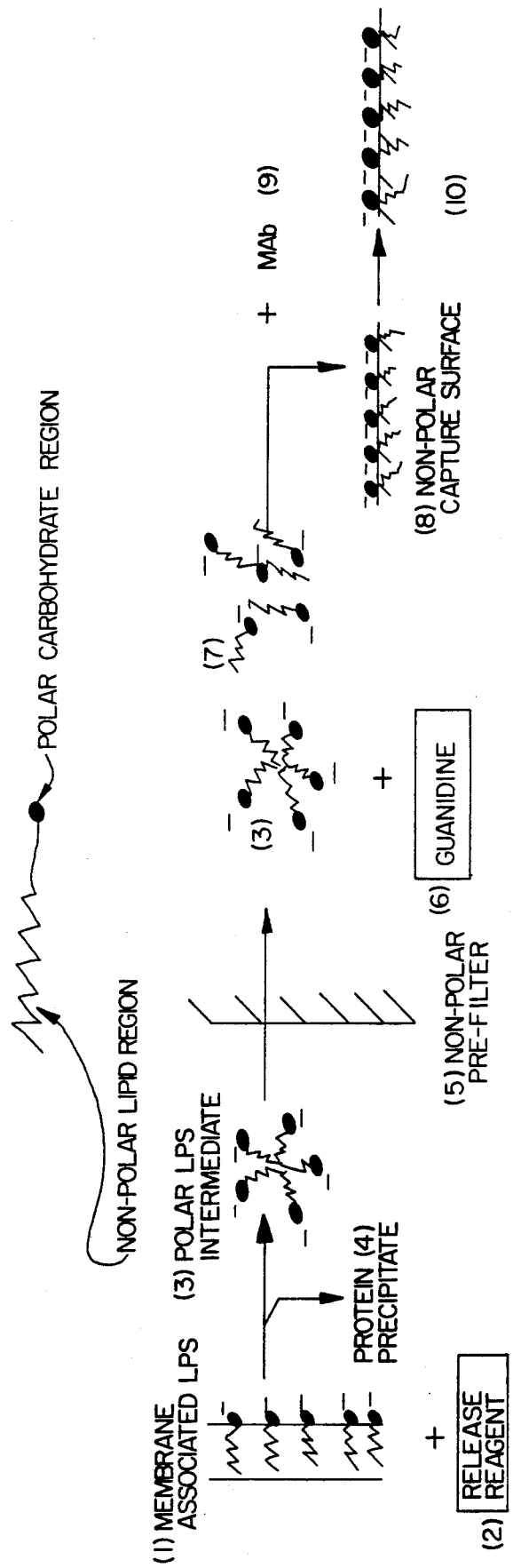
FIG. 2 schematically illustrates a preferred practice of the invention.

As shown in FIG. 1, the analyte is a LPS molecule derived from *C. trachomatis*. In native form this analyte exists as a membrane associated complex 1 and possesses poor affinity for the capture surface of choice as shown in FIG. 1. The membrane of complex 1 is disrupted by treatment with a release reagent 2. A polar LPS intermediate 3 is released from the membrane complex 1 and is in such a conformation that the non-polar lipid region is not free to bind with the surrounding matrix. A micellular structure such as that shown at 4 is one such configuration consistent with the observed chemical properties. Other conformations may result. The precise structure formed under the described conditions is no material to the invention and is not known. Under these conditions described, protein and other matrix materials 5 which may be present in typical clinical specimens, are denatured and/or precipitated, or otherwise rendered non-interfering. Further, mucopolysaccharides and other mucoid substances, which may be present, are dispersed and rendered non-interfering. The non-polar pre-filter 5 mechanically or chemically removes many of these interfering substances. This pre-filter may be formed from materials such as high density polyethylene, Nylon of various formulations, glass fiber, or polysulfone. The preferred composition is a microporous high density polyethylene depth filter with an effective pore size of <1 micron. The analyte (LPS) is in a nonreactive configuration with the pre-filter. Therefore, analyte loss on the pre-filter is minimal.

The polar (LPS) intermediate is rendered non-polar by exposure to reagent 6 (e.g., guanidine, 3.6M, final concentration). Other reagents useful for this purpose may include urea and magnesium and perchloric acid. This non-polar form of the analyte binds by absorption into the non-polar capture surface 8 in such a manner that the analyte epitope is exposed and can be recognized by the appropriate detection reagents.

Interaction of the analyte (LPS) with a specific antibody, e.g., monoclonal antibody (MAB) 9, can be detected by known methods. The preferred detection method involves binding a biotinylated antibody with a streptavidin/$\beta$-galactosidase conjugate. This enzyme complex, following the reaction with a suitable chromogenic substrate provides a signal which is detectable by the eye or by an appropriate instrument. Other signal generators may be used in known manner.

The release reagent may appropriately be an aqueous solution containing from about 10% to 90% by weight of an aliphatic alcohol having from about 1 to 5 carbon atoms. Ethanol is preferred. Mixtures of alcohols may be utilized. The release reagent solution also preferably contains from about 0.030% to 0.600% by weight of a chelating agent such as ethylenediamine tetracetic acid (EDTA). The pH is preferable in the range of from about 9 to about 14. An appropriate pH may be provided by an alkali metal of hydroxide, e.g., sodium hydroxide. The preferred detergent is sodium deoxycholate, however, other ionic detergents may also be used. The release reagent should consist of 0.05% to 5.00% by weight of the appropriate detergent.

One release reagent useful in the invention may be prepared as follows:
(i) dissolve 38 g of EDTA in 370 ml of di $H_2O$
(ii) add 40 ml of 5 molar aqueous NaOH
(iii) add 50 ml of 10% sodium deoxycholate (DOCA)
(iv) add 340 ml of ethanol
(v) add 200 ml of N-butanol The second reagent renders the polar LPS intermediate non-polar. In the presence of an appropriate concentration, guanidine in aqueous solution, non-covalent bonds between membrane proteins, carbohydrate and other components (including LPS) are disrupted. Under these conditions, compounds exist in separate and freely soluble forms. The hydrophobic R-groups tend to become exposed in the presence of guanidine and are more likely to interactive with a hydrophobic surface such as the capture solid phase. Any reagent effective to impart polarity to the non-polar LPS intermediate may be used. A preferred reagent is an aqueous solution of from about 1.0M to about 7M, preferably 3.3 molar guanidine.

False positive reactions may be minimized or eliminated subjecting the LPS antibody to be used in the immunoassay to the procedure and protocol substantially as described in O'Shannessy and Quarles J. Applied Biochem 7:347–355 (1985) and O'Shannessy and Quarles J. Immunological Methods 99:153–161 (1987).

This invention provides an enzyme immunoassay of improved sensitivity and specificity for amphipathic analytes. This improvement is illustrated by the following comparative example in which Part A describes a prior art procedure and Part B describes an assay conducted pursuant to this invention. Table I sets forth the data observed in the Part A and Part B experiments.

PART A AQUEOUS PROCEDURE
EXAMPLE 1

| | Reagent Description |
|---|---|
| Reagent A = | 100 μg/ml proteinase K solution in 10 μM aqueous sodium phosphate, pH 7.75. |
| Reagent B = | 0.25% (w/v) sulfated polystyrene beads 1–2 microns in diameter. |
| Reagent C = | 400 mM aqueous trisodium phosphate |
| Reagent D = | 750 mM aqueous sodium phosphate (monobasic), 6M aqueous guanidine hydrochloride |
| Reagent E = | Protein A purified murine anti-chlamydia LPS IgG. |
| Reagent F = | Goat anti-mouse IgG conjugated to alkaline phosphatase (commercial product available from Scripps Laboratories) |
| Reagent G = | 4 mM 5-bromo-4-chloro-3-inolylphosphate sodium salt (BCIP) |
| Stop Solution = | 1 molar monobasic sodium phosphate |
| Wash Solution = | isotonic phosphate buffered saline, 0.1% (v/v) tween 20 |

Chlamydia Assay Protocol for Part A

A. Preparation of Positive Control (Whole chlamydia elementary bodies, 4,000/ml)

1. Vortex positive control for 30 seconds.
2. Add 2 drops Positive Control to 1 ml of aqueous specimen dilution buffer.
3. Add 1 drop Reagent A and 1 drop Reagent B.
4. Vortex for 15 seconds.

B. Preparation of Patient Swabs

5. To the swab add 1 ml of specimen dilution buffer (10 mM sodium phosphate, 10 mM n-acetyl-cysteine, 250 mM NaCl, 0.62% deoxycholic acid, pH 7.25). Incubate for 5 minutes. Add 1 drop of Reagent A and 1 drop of Reagent B.
6. Vortex for 3 cycles of approximately 15 seconds each.
7. Remove the swab. Expel any excess liquid by pressing swab against the sides of the tube. Discard the swab.
8. Cap the tube with a new cap and incubate 30 minutes at 60° C.
9. Add 3 drops Reagent C, vortex, incubate 5 minutes.
10. Add 3 drops Reagent D, vortex, incubate 5 minutes.
11. Decant over device with funnel in place. If sample does not flow through in 5 minutes reject sample.
12. Fill reservoir with approximately 1 ml Wash Solution. Let drain. Repeat.
13. Add 5 drops Reagent E, incubate 5 minutes.
14. Add 5 drops Reagent F, incubate 5 minutes.
15. Fill up reservoir with Wash Solution. Let drain.
16. Slide back the funnel and fill the reservoir once (Wash Solution).
17. Add 5 drops Reagent G (Substrate Solution) dropwise, -continued

PART A AQUEOUS PROCEDURE
EXAMPLE 1 incubate 5 minutes.
18. Stop reaction with 0.5 ml of Reagent H (Stop Solution).

Part B - Alcohol and Guanidine Procedure
Reagent Description for Part B:

Reagent A = Release reagent (34% ethanol, 20% butanol, 46% water, 0.5% Deoxycholic acid HCl, 0.2M NaOH, 0.1% EDTA)
Reagent B = 7.2M guanidine HCL
Reagent C = Wash (isotonic phosphate buffered saline, 0.1% v/v tween 20)
Reagent D = Detect antibody (biotinylated murine antichlamydia LPS monoclonal IgG)
Reagent E = Detect conjugate (streptavidin β-galactosidase)
Reagent F = Enzyme substrate (Chlorophenol red β-galactopyranoside)
Reagent G = 4 mM 5-bromo-4-chloro-3-inolylphosphate sodium salt (BCIP)

Protocol for Part B

1. Add 1.0 ml Reagent A to transport tube, vortex 3 times for 10 seconds, incubate 5 minutes.
2. Vortex transport tube 3 times for 10 seconds, repeat procedure if necessary to remove mucus.
3. Remove brush while squeezing against the sides.
4. Insert filter plunger into the transport tube and depress gently.
5. Dispense 1.0 ml Reagent B to the top of the plunger, vortex 3 times for 5 seconds.
6. Dispense into the funnel on the test device and allow the fluid to completely absorb.
7. Fill funnel with Wash Reagent C, slide funnel aside and fill tray with Wash Reagent C, each time allowing for complete absorption.
8. Add 3 drops Antibody Reagent D to the center of the capture membrane, one drop at a time, incubate 4 minutes.
9. Add 3 drops Reagent E to the center of the capture membrane, one drop at a time, incubate 1 minute.
10. Fill the tray with Wash Reagent C, allow to completely soak in then fill the tray a second time.
11. Add 2 drops Reagent F to the center of the capture membrane one drop at a time, incubate 5 minutes.
12. Read results.

Table 1 compares a non-alcohol aqueous release reagent with an alcohol ethanol containing release agent which incorporates guanidine

TABLE 1

| release reagent type | sensitivity | specificity | incidence | n |
|---|---|---|---|---|
| aqueous (Part A) | 46% | 86% | 10.3% | 232 |
| alcohol + guanidine (Part B) | 79% | 97% | 17.0% | 473 |

Data was obtained from two separate studies utilizing direct patient specimens Sensitivity means total number of diagnostic positives divided by the total true positives as defined by culture. Specificity means total number of diagnostic negatives divided by the total true negatives as defined by culture. Incidence means total true positives divided by n multiplied by 100. "n" stands for the total number of specimens tested.

We claim:

1. An immunoassay for the detection of an amphipathic analyte which comprises
   treating a sample which may contain said analyte with a release reagent to release said analyte from background matrix material with which it may be associated wherein said release reagent comprises an aqueous solution of an alcohol having from 2 to about 5 carbon atoms;
   separating the released analyte from said matrix material; and
   treating the separated, released analyte with a second agent to render it reactive with a capture surface, wherein said second reagent comprises guanidine in an aqueous solution.

2. An immunoassay as defined by claim 1 in which the amphipathic analyte is a lipopolysaccharide of *chlamydia trachomatis* or *chlamydia psittaci*.

3. An immunoassay as defined by claim 1 or claim 2 in which said release reagent consists essentially of ethanol, butanol, a chelating agent a detergent and water and said second reagent consists essentially of guanidine hydrochloride in aqueous solution.

4. An immunoassay for the detection of an amphipathic analyte included in matrix material which may yield interfering background in said assay which comprises
   (i) treating a sample which may contain said analyte with a release reagent to release said analyte from said matrix material and to provide a polar, released analyte intermediate
   said release reagent consisting essentially of a buffered alcohol having from 1 to about 5 carbon atoms, a detergent and a chelating agent
   (ii) separating said polar, released analyte intermediate from said matrix material
   (iii) passing said polar, released analyte intermediate through a non-polar filter to remove additional matrix material if present
   (iv) thereafter treating said polar, released analyte with a second reagent to render the released analyte non-polar
   said second reagent consisting essentially of a guanidine hydrochloride solution
   (v) binding said non-polar released analyte to a non-polar capture surface.

5. An immunoassay as defined by claim 4 in which the amphipathic analyte is a lipolysaccharide from *Chlamydia trachomatis*.

* * * * *